United States Patent
Hirano

[19]

[11] Patent Number: 5,836,997
[45] Date of Patent: Nov. 17, 1998

[54] SYSTEM FOR PREVENTING AND CURING OSTEOPOROSIS AND OBESITY

[75] Inventor: Shinnosuke Hirano, Kanagawa, Japan

[73] Assignee: Kohgen Kizai Kabushiki Kaisha, Yokohama, Japan

[21] Appl. No.: 755,659

[22] Filed: Nov. 25, 1996

[30] Foreign Application Priority Data

Apr. 3, 1996 [JP] Japan ................................. 8-104734

[51] Int. Cl.$^6$ .................................................... A61N 1/20
[52] U.S. Cl. ............................................. 607/75; 607/152
[58] Field of Search .................................. 607/2, 75, 152

[56] References Cited

U.S. PATENT DOCUMENTS 5,520,180   5/1996   Uy et al. .................................. 607/152

FOREIGN PATENT DOCUMENTS

| 4-5823(A) | 1/1992 | Japan . | |
|---|---|---|---|
| 4-16665(B) | 4/1992 | Japan . | |
| 0196814 | 6/1938 | Switzerland | 607/2 |
| 2164563 | 3/1986 | United Kingdom | 607/2 |

*Primary Examiner*—William E. Kamm
*Attorney, Agent, or Firm*—Nikaido, Marmelstein Murray & Oram LLP

[57] ABSTRACT

A system for preventing and curing osteoporosis and obesity, which has a mat essentially consisting of a first sheet made from a semiconductive or insulating material and having a volume resistivity of less than $10^4$ $\Omega$.cm and a second sheet made from a semiconductive or insulating material, laminated on the first sheet and having a volume resistivity of $10^4$ $\Omega$.cm or more; an electric power source; an electrical circuit to apply DC voltage of 25–800 to the first sheet; and a control unit. A normal person or patient is made contact with the mat, so as to put his body in electrostatic field to be formed on the mat. In another embodiment, a third sheet of a material having a volume resistivity of more than $10^{12}$ $\Omega$.cm is used such that the first sheet is sandwiched between the third and second sheets.

3 Claims, 8 Drawing Sheets

1 μm

1 μm

SYSTEM FOR PREVENTING AND CURING OSTEOPOROSIS AND OBESITY

BACKGROUND OF THE INVENTION

1. Field of the Invention

The present invention relates to a system for preventing and curing osteoporosis and obesity, by putting a human body in an electrostatic field.

2. Related Art

In recent years, medical techniques have greatly advanced to prolong the average span of human life and as a result, so-called "adult and senior diseases" tend to increase. Therefore, it has been emphasized in the medical world that so-called "Health medical science" will be required, in which each individual controls his health by himself to prevent a disease or pays his possible effort to overcome the diseases.

Among the diseases, osteoporosis has often been found in senior persons and women in menopause and it has been said that number of the patients with this disease reaches 6 million or more, even in Japan only.

It has been known that osteoporosis causes lumbago and fracture of bone due to extreme reduction in amount of calcium and other mineral components constituting the bone, but its preventing and curing method has not been known other than in-take of foods containing calcium, vitamin D and others, solar bath and physical exercise.

For preventing and/or curing obesity, while, there is no measure other than abstaining from excess intake of high calorie food and drink and taking proper physical exercise.

Turning now to human health, various studies has been widely made on water, as interests increases on relations between body fluids such as blood and human health, environmental pollutions and foods, and the like. Through such studies, it has been found that water suitably permeates into human cell to activate the same, when a large cluster consisting of connected chain of water molecule is made into small clusters with a short chain length. It has been known that magnetic energy and extreme infrared rays are effective for dividing the cluster.

Therefore, various devices utilizing such a principle have been proposed. For instance, in Japanese Utility Model 4-16665(B), there is disclosed a healthy mat utilizing magnetic energy and extreme infrared rays. While, in Japanese Utility Model 4-5823(A), there is disclosed another healthy mat, wherein a heating wire is arranged on a non-woven fabric base layer and sandwiched with a pair of adhesive sheets to provide electric potential therapy and thermotherapy.

Recently, such a fact has been watched with an interest that action of static electricity is very effective for dividing the large cluster of water molecule and thus an electric potential therapeutic device has been developed. According to the device, high voltage of several hundred to several thousand volts is applied to a single electrical insulation sheet or mat made from vinyl chloride or the like synthetic resin to induce the static electricity.

All of such devices have been utilized to relieve headache and shoulder stiffness as well as to prevent and cure insomnia and chronic constipation. Among the devises, those utilizing magnetic energy and/or extreme infrared rays are not sufficient in effectiveness. While, the device utilizing static electricity requires incidental facilities for increasing voltage such as a large transformer, so that it becomes larger in size to increase manufacturing and running costs. Further, the device has a serious disadvantage of that a user might get a shock of electricity due to leakage thereof.

In order to overcome the disadvantages of the device utilizing static electricity, one of the researchers in the assignee company has studied to find facts that static electricity can be stably induced, if laminating a first sheet of conductive or semiconductive layer having a volume resistivity of less than $10^4$ Ω.cm to a second sheet of conductive or insulation layer having a volume resistivity of $10^4$–$10^{12}$ Ω.cm, and applying voltage to the first sheet, that a value of electrostatic volt can be made higher level, if the difference in volume resistivity of the first and second sheets is set to $10^4$ Ω.cm or more, and that a possibility of the dangerous shock due to leakage of electricity can be avoided by setting voltage and current to be applied to the first sheet to 25–800V and 0.8 mA, respectively. The assignee company has filed a patent application in Japan under number of 249185/1995 on the invention, based on such findings. According to the device disclosed in the specification for the Japanese patent application, it is possible to induce electrostatic voltage of −3.05 KV on the second sheet having a volume resistivity of $10^7$ Ω.cm by applying 800V to the first sheet having a volume resistivity of $10^3$ Ω.cm, and this device is suitable for relieving headache and shoulder stiffness as well as preventing and curing insomnia and chronic constipation.

By using the device, the inventor has energetically studied and investigated on influence(s) of the static electricity to a living body through tests using experimental animals to seek a new application use(s) of it. As a result, it has been unexpectedly found that the device is useful for inhibiting a decrease in an amount of bone to prevent and cure osteoporosis and also inhibiting an appetite without increasing a body weight to prevent and cure obesity, so that the invention was established.

SUMMARY OF THE INVENTION

Therefore, an object of the invention is to provide a system for preventing and curing osteoporosis and obesity, by putting a human body in an electrostatic field, for instance contacting the body with a mat which is inducing static electricity.

According to the invention, the object is attained by a system for preventing and curing osteoporosis and obesity, which comprises a mat essentially consisting of a first sheet made from a semiconductive or insulating material and having a volume resistivity of less than $10^4$ Ω.cm and a second sheet made from a semiconductive or insulating material, laminated on said first sheet and having a volume resistivity of $10^4$ Ω.cm or more; an electric power source; an electrical circuit to apply DC voltage of 25–800 to said first sheet; and a control unit.

The first and second sheet are made from one of silicone rubber, natural rubber, nitrile rubber and synthetic resin material (such as vinyl chloride and polyurethane resin) and carbon. The second sheet may contain a ceramic material such as fine particles of granite radiating extreme infrared rays having wavelength of 4–14 μm, which shows an action for dividing the cluster of water molecules.

It is preferable to set the electrical output for the first sheet as 800V and 0.8 mA.

DESCRIPTION OF THE PREFERRED EMBODIMENTS

The invention will now be further explained with reference to drawings.

Figure 1:
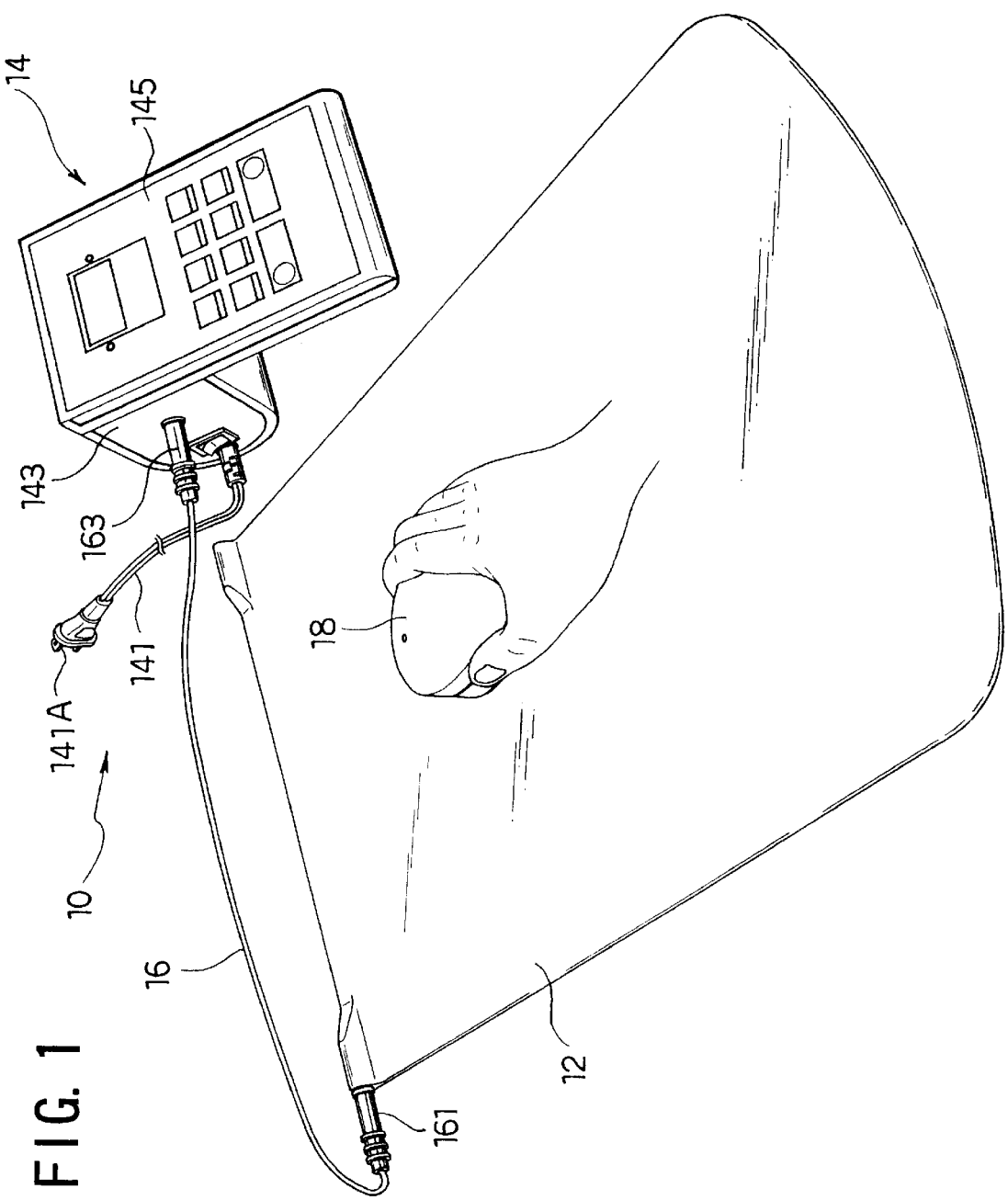
FIG. 1 is a schematic and perspective illustration showing a system according to the invention.

In FIG. 1, there is shown a system 10 according to the invention. The system 10 comprises a mat 12, a control unit 14, a cable 16 with jacks 161 and 163 connecting the mat 12 with the control unit 14, and a sensor 18 for static electricity. The control unit 14 has a cable 141 with a plug 141A which is to be electrically connected with a plug receptacle (not shown) for commercial voltage source, a main part 143, and an operating board 145.

Figure 2:
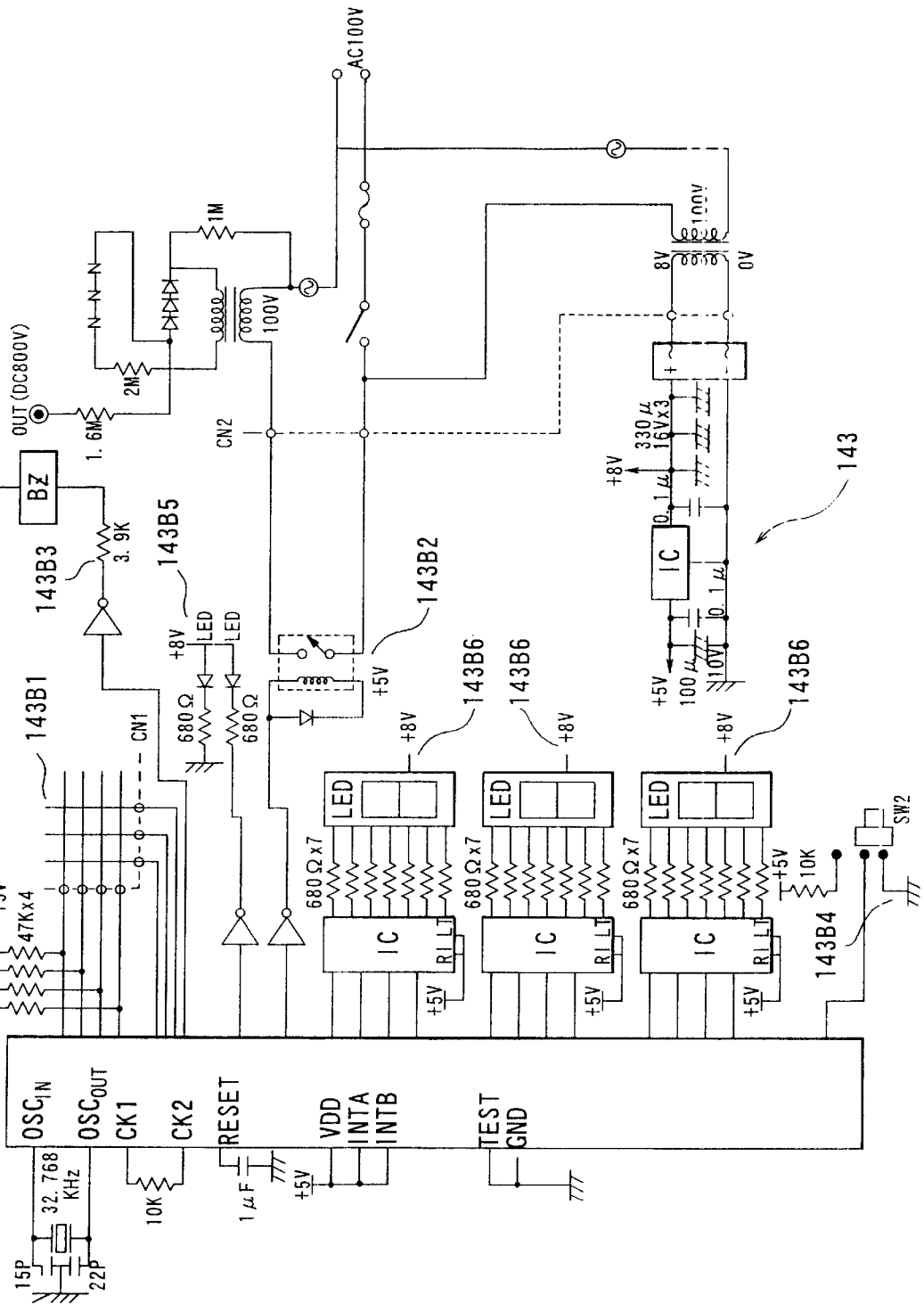
FIG. 2 shows an electrical circuit for a transforming section and operation section in a control unit of the system shown in FIG. 1.

FIG. 2 show an electric circuit for the main part 143 which has a transforming section 143A and an operating section 143B. The transforming section transforms AC 100V from the commercial voltage source into DC 800V which appears at J1 and supplied to the mat 12 through the connecting cable 16, DC 5V which is supplied to a basic operating circuit 143B1, an electromagnetic circuit 143B2, a buzzer circuit 143B3 and a timer mode switching circuit 143B4, and DC 8V which is supplied to a lamp circuit 143B5, and timer and display circuits 143B6.

Figure 3:
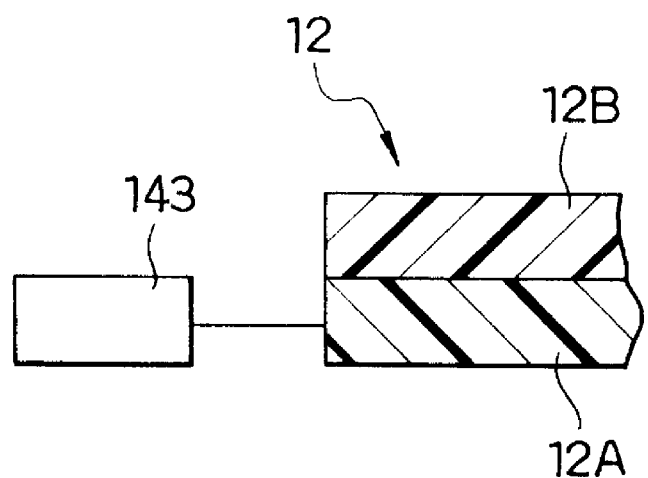
FIG. 3 is a schematic and sectional illustration of a mat for the system shown in FIG. 1, which shall induce static electricity.

The voltage increased to 800V by the transforming section 143A and appeared at output terminal J1 is applied to a first sheet 12A of the mat 12 to uniformly generate static electricity on surface of a second sheet 12B laminated on the first sheet 12A (see FIG. 3). In this case, a value of current should be set to a small one, for instance 0.8 mA, to avoid leakage and shock of electricity.

Results shown in following Table 1 were obtained, when the first and second sheets having various volume resistivity were laminated and DC 800V (0.8 mA) was applied to the first sheet to check electrostatic voltage induced on the sheets.

TABLE 1

| Volume resistivity ($\Omega \cdot cm$) | | Electrostatic voltage (-KV) | |
|---|---|---|---|
| First sheet | Second sheet | First sheet | Second sheet |
| $10^3$ | $10^7$ | 0.01 | 3.05 |
| $10^2$ | $10^{10}$ | 0.01 | 2.30 |
| $10^5$ | $10^{10}$ | 0.02 | 0.87 |
| $10^5$ | $10^6$ | 0.03 | 0.03 |

It is apparent from the results that the volume resistivity of the first and second sheets should be set to $10^2$–$10^4$ and $10^6$–$10^{10}$ $\Omega.cm$, respectively, that difference in the volume resistivity of the first and second sheets should be set to $10^4$ $\Omega.cm$ or more, and that such a case is best that the volume resistivity of the first and second sheets is $10^3$ and $10^7$ $\Omega.cm$, respectively.

Figure 4:
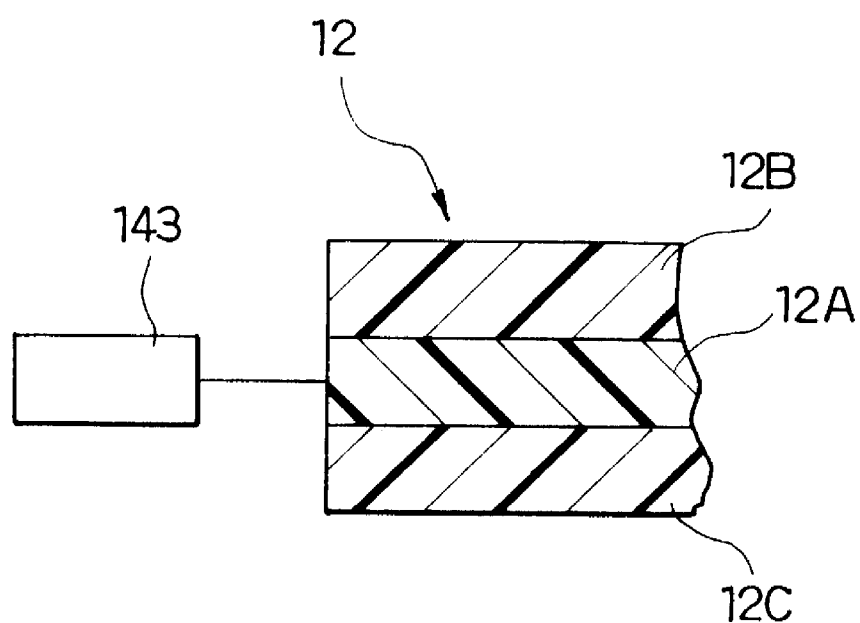
FIG. 4 is a schematic and sectional illustration showing another embodiment of the mat as in FIG. 2.

As shown in FIG. 4, the mat 12 may have an additional sheet 12C, in addition to the sheets 12A and 12B as in FIG. 3, but please note that the sheet 12C has been made from a material having a volume resistivity of more than $10^{12}$ $\Omega.cm$ or electrical insulation substance.

Although the mat 12 have been exaggeratedly illustrated in FIGS. 3 and 4, please note that thickness of each sheet is of about 1 mm.

EXPERIMENTAL TESTS (1) Object

By using a rat model imitating an estrogen deficient symptom which appear with a specificity to women normally living under a pleasant environment and an intake a sufficient food and drink to elucidate a generation mechanism of obesity and osteoporosis often found in such women and check an action of static electricity by using the system as said above.

(2) Experimental animals

SD female rats (9 weeks old) were bred for 27 days to inure the same, selected healthy animals, classified into following 4 groups and subjected to a sham operation or ovariotomy under anesthesia with nembutal (pentobarbital sodium).

(A) Sham group (8 animals): Animals subjected to a sham operation, only.

(B) Sham+ZZ group (8 animals): Animals subjected to a sham operation and then treated by the system according to the invention.

(C) OVX group (8 animals):
Animals subjected to ovariotomy.

(D) OVX+ZZ group (8 animals):
Animals subjected to ovariotomy and then treated by the system according to the invention.

(3) System according to the invention and method of treating the animals by the system The system as shown in FIG. 1 was used. A mat for the system is three-layered one consisting of a first or middle sheet of a silicone rubber with carbon black (manufactured by Toshiba Silicone Co., Ltd. as "XE23-B1717") having a volume resistivity of about $10^3$ $\Omega.cm$, second or upper sheet of a silicone rubber (manufactured by Toray, Dow Corning and Silicone Co., Ltd. as "SE4635U") having a volume resistivity of about $10^7$ $\Omega.cm$) and third or lower sheet of a silicone rubber (manufactured by Toshiba Silicone Co., Ltd. as "TSE221-3U") having a volume resistivity of more than $10^{12}$ $\Omega.cm$).

Specification of the system is as follows.
  (i) Rated voltage: 100V
  (ii) Output voltage: 800V
  (iii) Frequency: 50/60 Hz
  (iv) Consuming power: 6 W
  (v) Body portion: Size: 111 (height)×104 (width)×177 (depth) mm Weight: 1,100 g
  (vi) Mat portion: Size: 3 (thickness)×500 (length)×350 (width) mm Weight: 760 g The system induces electrostatic voltage of −3.05 KV on the mat.

The system was operated and then a stainless-steel cage, each accommodating 4 animals, was mounted on the mat of the system to treat the experimental animals for 2 hours from P.M. 1:00 −3:00 over 5 days/week and for 7 weeks.

(4) Preparation of specimen

After the operation, the animals in each group were bred for 7 weeks under a day and night cycle of 12–12 hours by an illumination, in constant temperature (24°±0.5° C.) and humidity (45–50%) conditions. The animals had freely taken their feed ["MF pellets" (Trade mark) manufactured by Oriental Yeast Co., Ltd. of Tokyo, Japan] and drinking water (distilled water), through the experimental period of time.

An intake amount of feed and body weight of each animal were measured at intervals through the experimental period of time.

After lapsed 7 weeks from the operation, each animal was killed under chloroform vapor atmosphere to cut off a right leg. Each of right leg tibia removed meat therefrom was ground by a grindstone while washing with water to obtain a vertical sectional specimen.

(5) Statistical processing

Some of the experiments were carried out 3–5 times. A statistical examination was carried out by ANOVA or Scheffe's Test and indicated by mean value±SD.

(6) Item of experiments (A) Intake amount of feed and change in body weight (B) Measurement of bone density A bone density of each specimen was quantitatively measured by CDX method using a computer soft of "Bonalyzer" (Trademark) marketed from Teijin Ltd. of Tokyo, Japan. Namely, An X-ray photograph of the specimen was taken together with an aluminum reference under conditions of 4 mA, 40 cm, 120 seconds and 35 kV. The bone mineral density was read out by a personal computer (Model PC-9801 manufactured by NEC Corporation of Tokyo, Japan), based on an image of the X-ray photograph. As an index of the bone density, following formula was employed.

$$\Sigma GS/D \ (mmAl)$$

wherein

ΣGS: Total amount of bone, and

D: Diameter of tibia.

(C) Observation of bone near the tibia

The specimen vacuum evaporated with carbon was observed by a scanning type electron microscope (Model ERA-8000FE manufactured by Elionics Co., Ltd. of Tokyo, Japan) under conditions of 20 mA and 20 kV.

(7) Results (A) Intake amount of feed and change in body weight (a) Intake amount An intake amount of feed in each group is shown in following Table 2. As apparently seen therefrom, An intake amount in Sham+ZZ group increases 22% in comparison with that in Sham group, but no significant difference can be recognized between OVX and OVX+ZZ groups.

TABLE 2

| Group | Intake amount (g/day/rat) |
|---|---|
| Sham | 17.5 ± 1.6 |
| Sham + ZZ | 21.3 ± 1.7* |
| OVX | 21.1 ± 1.7* |
| OVX + ZZ | 20.6 ± 1.7* |

*: p < 0.05

(b) Change in body weight

Figure 5:
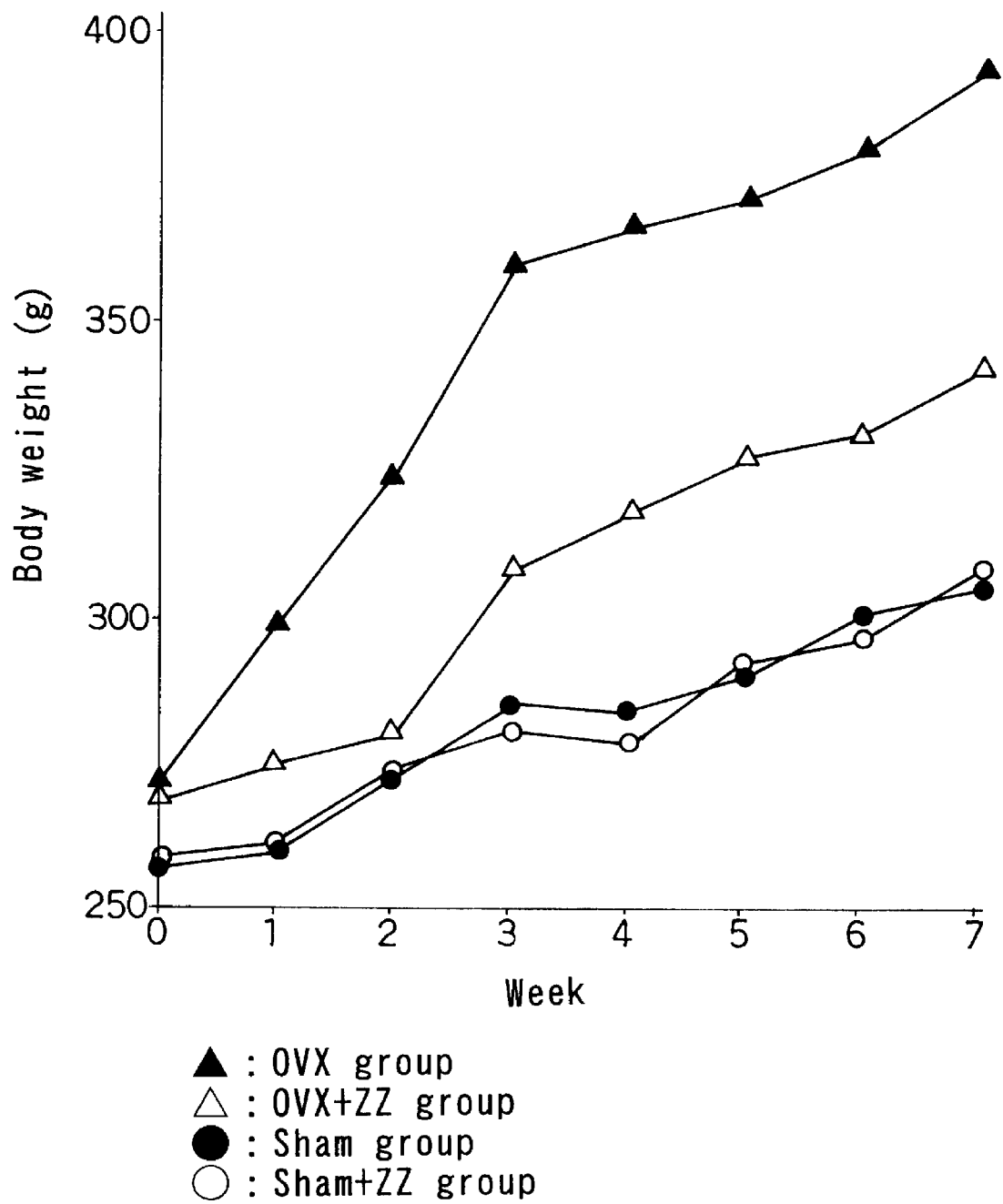
FIG. 5 is a graph showing a relation between breeding period of time and change of body weight of animals.

Results are shown in FIG. 5. As apparently seen therefrom, an increase in body weight is not different between Sham and Sham+ZZ groups, but an inhibition of about 15% was observed in OVX+ZZ group in comparison with OVX group.

(B) Bone density

Results are shown in following Table 3.

TABLE 3

| Group | Bone mineral density (Σ GS/D) |
|---|---|
| Sham | 1.00 ± 0.02 |
| Sham + ZZ | 1.03 ± 0.02 |
| OVX | 0.80 ± 0.02 |
| OVX + ZZ | 0.85 ± 0.02 |

(C) Observation by electron microscope

A portion near tibia of the specimens recognized a difference in bone density was observed by the scanning electron microscope (×12). FIGS. 6A, 6B, 6C and 6D are photographs thereof on Sham, Sham+ZZ, OVX and OVX+ZZ groups, respectively.

Figure 7A:
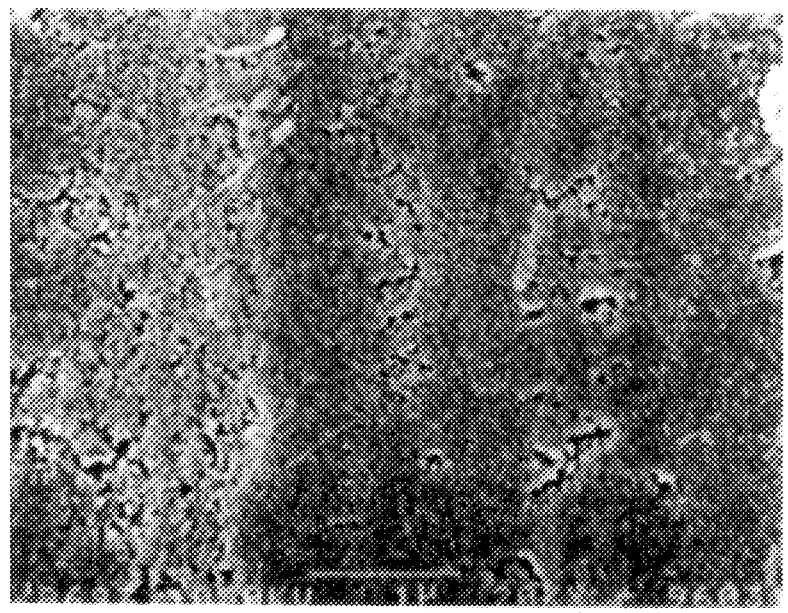
FIGS. 7A–7D is a photograph showing a part of the right tibia shown in FIGS. 6A–6D but taken by the electron microscope (×20,000).
Figure 7B:
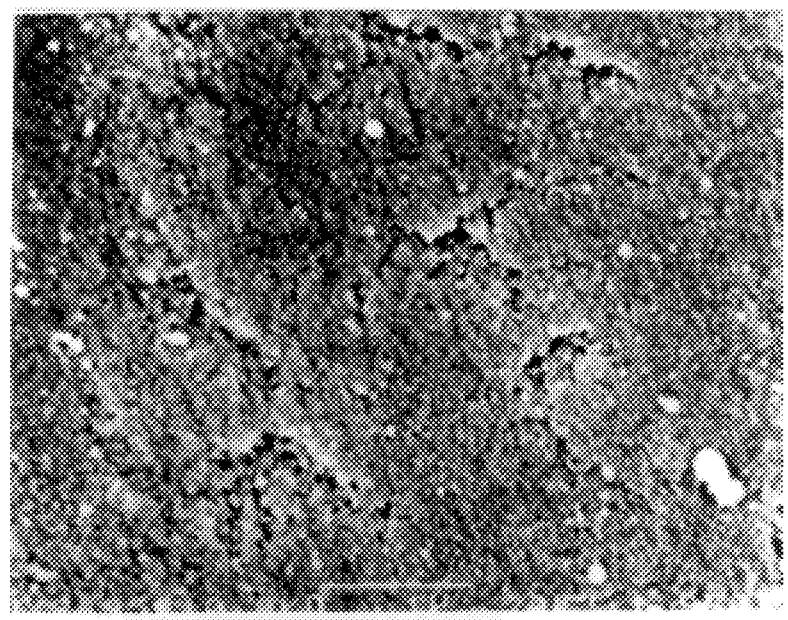
Figure 7C:
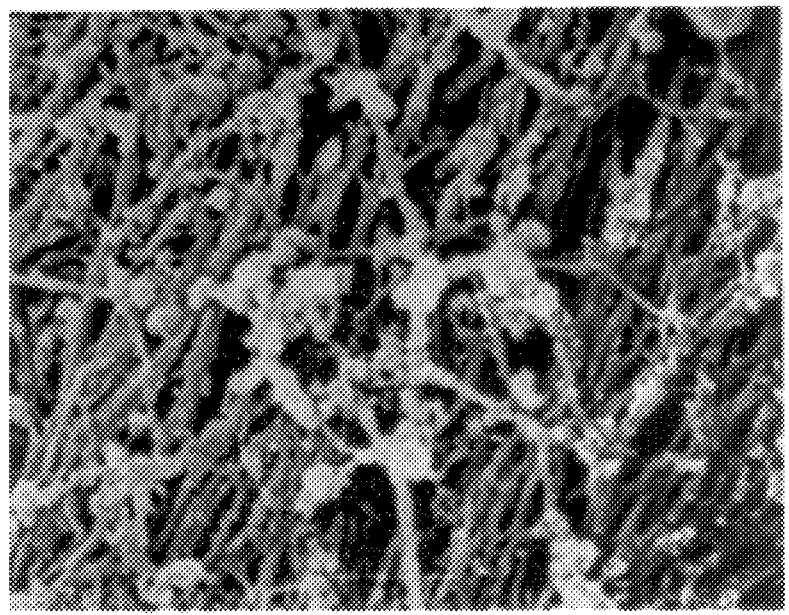
Figure 7D:
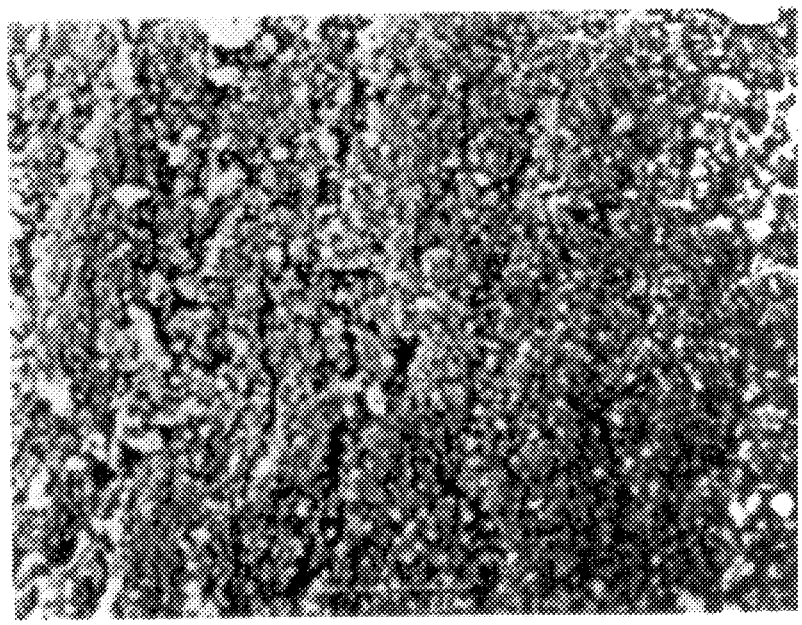

A surface structure of optionally selected spongy bone was similarly observed by the scanning electron microscope (×20000) and photographs thereof are shown in FIGS. 7A (Sham group), 7B (Sham+ZZ group), 7C (OVX group) and 7D (OVX+ZZ group). It is apparent that a surface of the spongy bone in OVX group (FIG. 7C) shows fibrous structure due to dissolution of the bone but in OVX+ZZ group (FIG. 7D), surface shows fine granular structure which is somewhat similar to that in Sham group (FIG. 7A), and there is no significant difference can be found in Sham group (FIG. 7A) and Sham+ZZ group (FIG. 7B).

Frequencies in appearance of fine granular, fibrous and intermediate structures are shown in following Table 4.

TABLE 4

| | Frequency in appearance | | |
|---|---|---|---|
| Group | Fine granular (%) | Intermediate (%) | Fibrous (%) |
| Sham | 24/24 (100) | 0/24 (0) | 0/24 |
| Sham + ZZ | 24/24 (100) | 0/24 (0) | 0/24 |
| OVX | 0/24 (0) | 3/24 (12.5) | 21/24 (87.5) |
| OVX + ZZ | 14/24 (58.3) | 8/24 (33.3) | 2/24 (8.3) |

(8) Consideration

The used rat model imitate estrogen deficient disease appeared with a specificity in women of the menopause. It has been well known that if the ovarium is exenterate, the model rat rapidly increases her body weight and causes the osteoporosis. The treatment according to the system of the invention can be expected to prevent and cure the obesity and osteoporosis from the results of experiments. It may be said that the treatment gives a certain influence to hormone (estrogen) system or its reaction system in vivo.

The treatment increases an appetite without increasing the body weight.

Figure 6A:
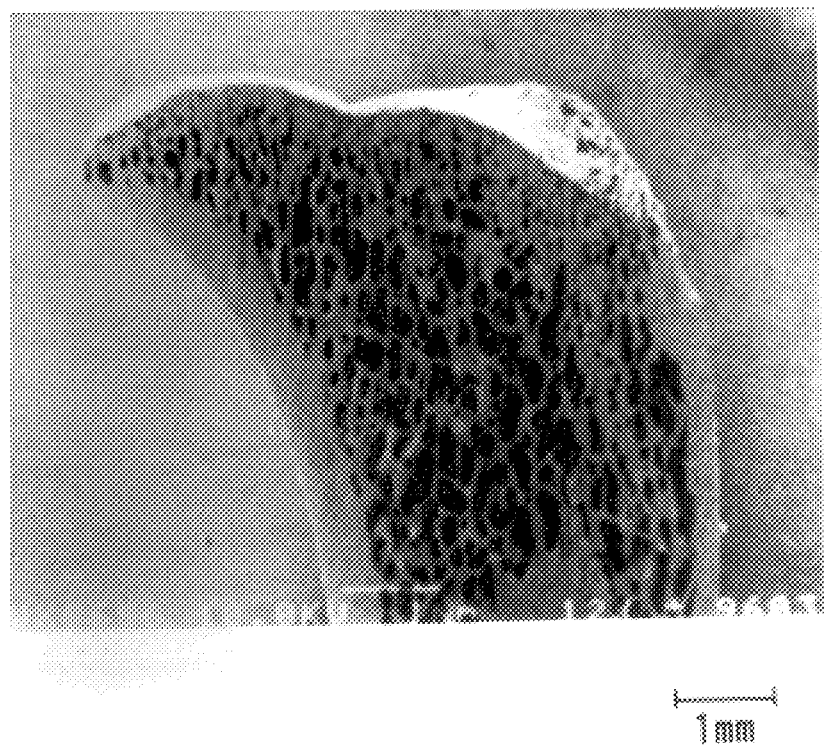
FIGS. 6A–6D shows a photograph of a right tibia taken by an electron microscope (×12), respectively.
Figure 6B:
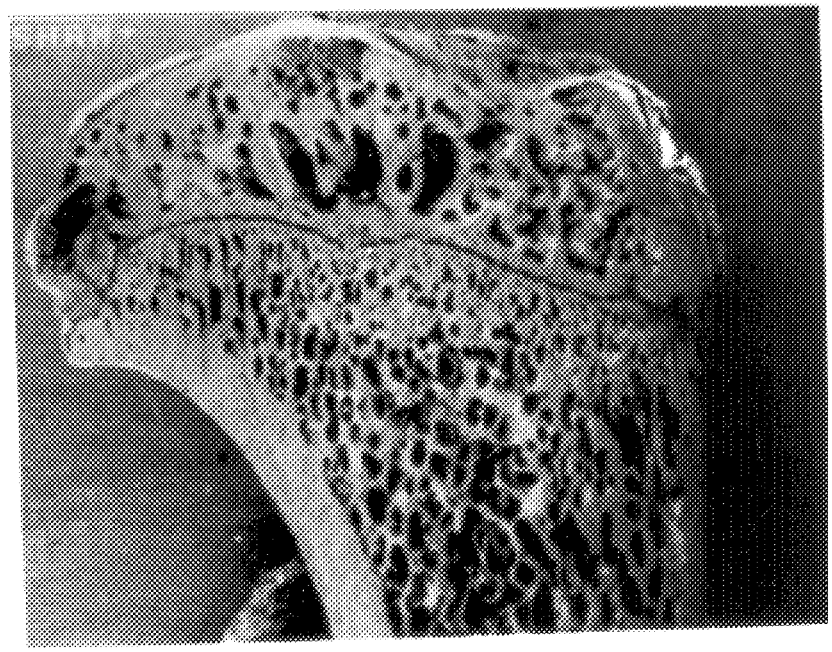
Figure 6C:
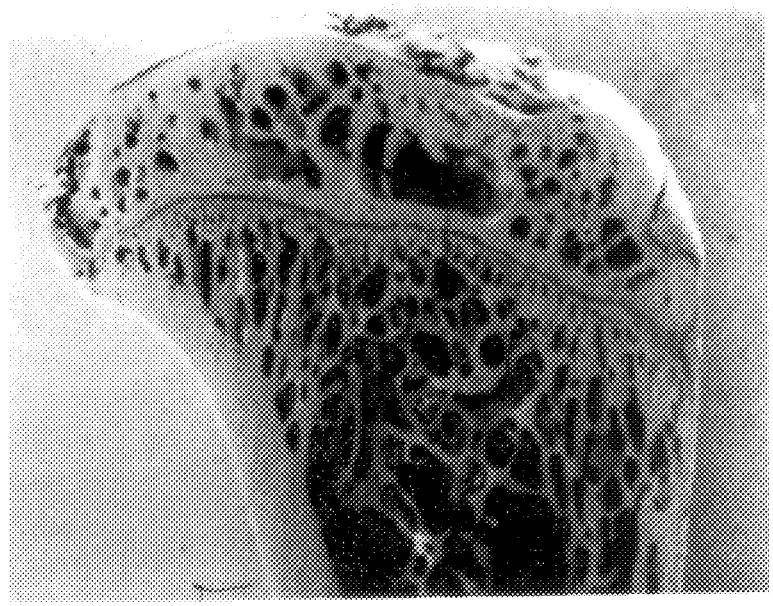
Figure 6D:
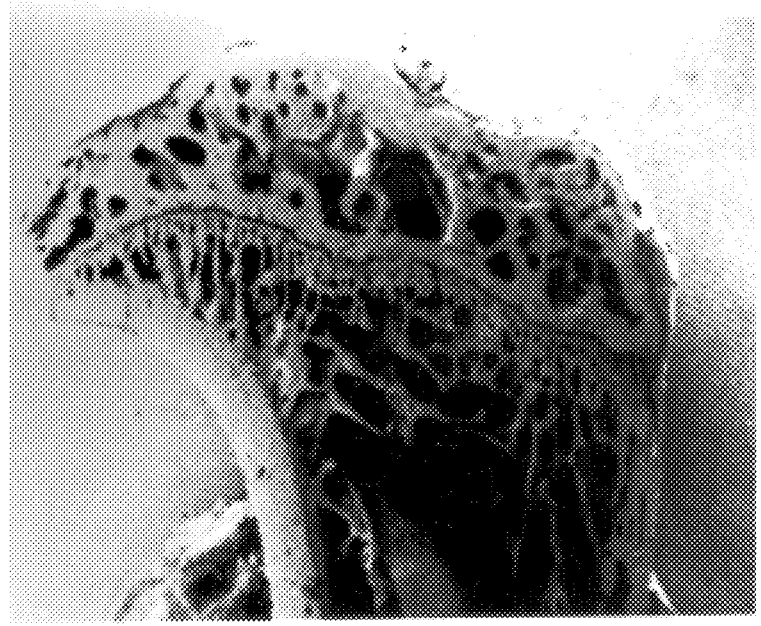

An osteoporosis with a decrease in number of bone beams causes, when the rat subjected to ovariotomy is bred for 7 weeks (see FIG. 6A and 6C). As to the fact that spongy bone becomes rough and shows a fibrous structure by dissolving in OVX group (see FIG. 7C), it shall be considered that in the rat subjected to ovariotomy, both of formation and absorption of bone accelerate and the absorption gain in power to cause a high rotational osteoporosis. Therefore, it can be considered that the modification of bone structure in OVX group (FIG. 7C) shows a result of calcium removal due to an acceleration of the bone absorption. Further, such a fact is very amusing that no apparent increase can be seen in spongy bone (see FIGS. 6C and 6D), but structure of the bone has been kept similar to that in Sham group by the treatment (see FIG. 7A and 7D) and such a fact has not been recognized between non-treated groups (Sham and OVX groups). Therefore, it seems to be that the treatment strongly inhibits a modification in bone structure.

What is claimed is:

1. A system for preventing and curing osteoporosis and obesity comprising a mat essentially consisting of a first sheet with a volume resistivity of less than $10^4$ $\Omega$.cm and a second sheet, laminated on said first sheet, having a volume resistivity of $10^4$ $\Omega$.cm or more; an electric power source having an electrical circuit to apply 25–800 VDC to said first sheet; and a control unit for controlling said electric power source.

2. A system as claimed in claim 1, wherein said first and second sheets have a volume resistivity of $10^3$ and $10^7$ $\Omega$.cm, respectively, and 800 VDC can be applied to said first sheet to induce an electrostatic voltage of −3.05 KV on said mat.

3. A system for preventing and curing osteoporosis and obesity comprising a mat essentially consisting of a first sheet with a volume resistivity of less than $10^4$ $\Omega$.cm, a second sheet laminated on said first sheet, having a volume resistivity of between $10^4 \Omega$ and $10^{12}$ $\Omega$.cm and a third sheet with a volume resistivity of more than $10^{12}$ $\Omega$.cm, wherein said first sheet is sandwiched between said second and third sheets; an electric power source having an electrical circuit to apply 25–800 VDC to said first sheet; and a control unit for controlling said electric power source.

* * * * *